United States Patent [19]
Frankel et al.

[11] Patent Number: 5,929,338
[45] Date of Patent: Jul. 27, 1999

[54] THICKNESS MEASUREMENT OF IN-GROUND CULVERTS

[75] Inventors: Julius Frankel, Rensselaer; Agostino Abbate, Clifton Park; Stephan C. Schroeder, Schenectady, all of N.Y.

[73] Assignee: The United States of America, as represented by the Secretary of the Army., Washington, D.C.

[21] Appl. No.: 09/062,190

[22] Filed: Apr. 17, 1998

[51] Int. Cl.⁶ .................................................. G01N 9/24
[52] U.S. Cl. ............................... 73/602; 73/620; 73/627
[58] Field of Search ........................... 73/644, 627, 602, 73/629, 622, 620, 597, 598, 609, 617

[56] References Cited

U.S. PATENT DOCUMENTS

| | | | |
|---|---|---|---|
| H1084 | 8/1992 | Bylenok et al. | 73/602 |
| 3,958,451 | 5/1976 | Richardson | 73/67.85 |
| 5,557,970 | 9/1996 | Abbate et al. | 73/597 |
| 5,741,962 | 4/1998 | Birchak et al. | 73/597 |

*Primary Examiner*—Hezron Williams
*Assistant Examiner*—Thuy Vinh Tran
*Attorney, Agent, or Firm*—John F. Moran; Michael C. Sachs

[57] ABSTRACT

A system which enables the user to measure continuously or intermittently or by remote command the thickness changes, above or below the water, under variable temperature changes of underground culverts with reliability. A liquid delay is used to couple the sound to the culvert comprising a focused transducer (10) screwed into a hollow cone-like structure called a "squirter" or "bubbler" (11) providing the operator of the system a means for searching for good echoes from which calculations of thickness with a computer can be made using the known velocity and echo return times.

2 Claims, 4 Drawing Sheets

THICKNESS MEASUREMENT OF IN-GROUND CULVERTS

U.S. GOVERNMENT INTEREST

The invention described herein may be manufactured, used, or licensed by or for the U.S. Government for U.S. Government purposes.

FIELD OF THE INVENTION

The present invention relates to a method and system for inspecting and measuring the wall thickness of culverts, providing a means to save unnecessary replacement expenditures and a means of preventing catastrophes. The present invention relates to an improved method of applying ultrasonic pulse-echo techniques.

BACKGROUND OF THE INVENTION

Key to the operation of the present invention, as in others mentioned herein, is the fact that sound waves propagate in isotropic or homogeneous materials in such a way that distance covered by the sound wave is linearly proportional to the time required. Thus, if the velocity is known and the return time of an echo is measured, the distance can readily be calculated with an accuracy or resolution, depending upon the measured qualities. Since velocities can be measured within one part in one thousand, $10^{-3}$, and time can be measured in nanoseconds, $10^{-9}$ seconds, or better, thicknesses may be measured to a resolution of $10^{-4}$ inches.

Prior art attempts to measure thicknesses of specimens such as gun barrels and the like are described in U.S. Pat. No. 5,182,139, in the name of J. Frankel and M. Doxbeck issued on Jan. 26, 1993. However, in that system it was not possible to enable the user to continuously or intermittently or by remote command in any time interval measure the thickness changes under conditions in which the temperature of the specimen changes.

The problems with the Frankel and Doxbeck patent were overcome by U.S. Pat. No. 5,557,970 in the name of A. Abbate, et al. issued on Sep. 24, 1996. In U.S. Pat. No. 5,557,970, as the sound wave is transmitted, the time for the sound wave to traverse the sample thickness and the first and second reference thicknesses is measured. Each standard includes a disk that is fluid coupled to a transducer. The thickness of the sample is determined by calculating the velocity of the signal from the traverse times for the first and second reference thicknesses. The calculations are performed by computer and are repeated over a period of time to calculate a change of thickness as a function of time. Simultaneously, thermocouples are attached to the sample being read by a temperature board whose data is fed into a computer. The computer monitors the output of the transducers and thermocouplers, and calculates the temperature compensated thickness or change in thickness as a function of time.

However, the above art does not solve the unique problems arising in the measurements on culverts.

Large culverts made of galvanized steel are used to allow water from a stream or river to flow from one side of a highway to the other. The water that flows through these culverts tends to corrode their interior. After the protective coating (the galvanizing) is gone, the underlying steel starts to corrode, and the wall thickness is reduced. A minimum wall thickness over a given region is needed in order for the culvert to remain capable of sustaining the weight of the earth and traffic above. These culverts have estimated safe lives which are based on rough experience since wall properties can vary. An unforeseen premature failure of a culvert due to corrosion can be the cause of injury or loss of life and at the very least extended traffic disruption. In spite of substantial costs, they are periodically replaced. The premature replacement of a culvert because of incorrectly perceived safety issues, i.e., perceived corrosion and therefore deterioration of wall thickness can present unneeded expenses. Thus an inspection technique with the reliable capability of measuring the wall thickness of culverts can be both a means to save unnecessary replacement expenditures (thus an impetus to preventive maintenance) and a means of preventing traffic catastrophes.

Ultrasonic pulse-echo techniques have been used to measure wall thicknesses to obtain an indication of the safety of culverts. This generally consists of an ultrasonic transducer being placed on a grease coated culvert wall and hooking it up to an electronic unit consisting of a pulser, a receiver, and a time counting circuit. The grease should allow for the ultrasonic wave generated by the transducer to propagate into the culvert wall. The electronic unit also has a numerical display which gives digital wall thickness readings. As the transducer is excited with a voltage pulse or spike, an ultrasonic pulse (main bang) is generated which traverses the bond, then enters the culvert wall, gets reflected on the opposite wall and returns to the transducer where a voltage is generated and the travel time is measured by the counting circuit in the electronic unit. The thickness of the culvert wall is then inferred by using the known sound velocity in the culvert using the fact that the velocity of the ultrasonic wave in the material times the travel time of the ultrasonic wave equals the distance traveled by the ultrasonic wave. The distance traversed by the ultrasonic wave in the material is twice the thickness of the material of interest.

Now the problems with the correct procedures are defined as follows:

The culvert wall thickness measurements must be taken in wet and dry conditions, but the grease which is used for bonding cannot be reliably applied and maintained under water.

When using contact transducers, the return time of the echo coming back from the opposite side of the culvert is so small, that part of it may fall within the recovery time of the main bang or voltage which signifies the initial excitation of the transducer. In this case the time measuring circuit produces erroneous readings, which the operator often cannot discern from valid ones.

The culvert often has an orange-peel like surface, which is a result of the corrosion that is taking place. The surface conditions preclude good bonding to a solid transducer and results in weak coupling and weak echoes, with ambiguous return times.

It is therefore difficult and impossible to obtain reliable readings above or below the water line when the culvert is corroded and in service using contact transducers.

Accordingly, it is an object of this invention to provide a method and system for measuring the wall thickness of culverts below and above their water line during the measurement process.

Another object of the invention is to provide a telemetry system which locates the position of the transducer when the thickness measurement is made allowing the record obtained at given time intervals to be compared and the required action taken, or measurement intervals determined.

Still another object of the invention is to provide a method in which a liquid delay is used to couple the sound to the culvert providing the operator a means for searching for a good echo.

Other objects will appear hereinafter.

SUMMARY OF THE INVENTION

It has now been discovered that the above and other objects of the present invention may be accomplished in the following manner by improving the existing techniques. The first change is to use a liquid delay to couple the sound to the culvert comprising a focused transducer which is screwed into a hollow cone-like structure called a "squirter" or "bubbler". Fluid is injected into the side of the squirter and exits in a stream at the tip of the cone, along its axis, which is coincident with the direction of propagation of the ultrasonic pulse emanating from the transducer. This fluid provides a path for the propagating ultrasonic wave. The searching for a good echo requires the technician to look at the ultrasonic signals on an oscilloscope. The technician then would adjust the position of the "squirter assembly" to maximize the echoes from the back surface of the culvert wall. The other feature of this invention is a telemetry system which locates the position of the transducer when the thickness measurement is made. This allows the thickness data and the position of the transducer in the culvert to be recorded and stored together to be plotted out at the end of the examination. This allows the record obtained at any given time interval to be compared and required action taken, or to determine measurement intervals.

BRIEF DESCRIPTION OF THE DRAWINGS

For a more complete understanding of the invention, reference is hereby made to the drawings, in which.

DETAILED DESCRIPTION OF THE PREFERRED METHOD

Figure 1:
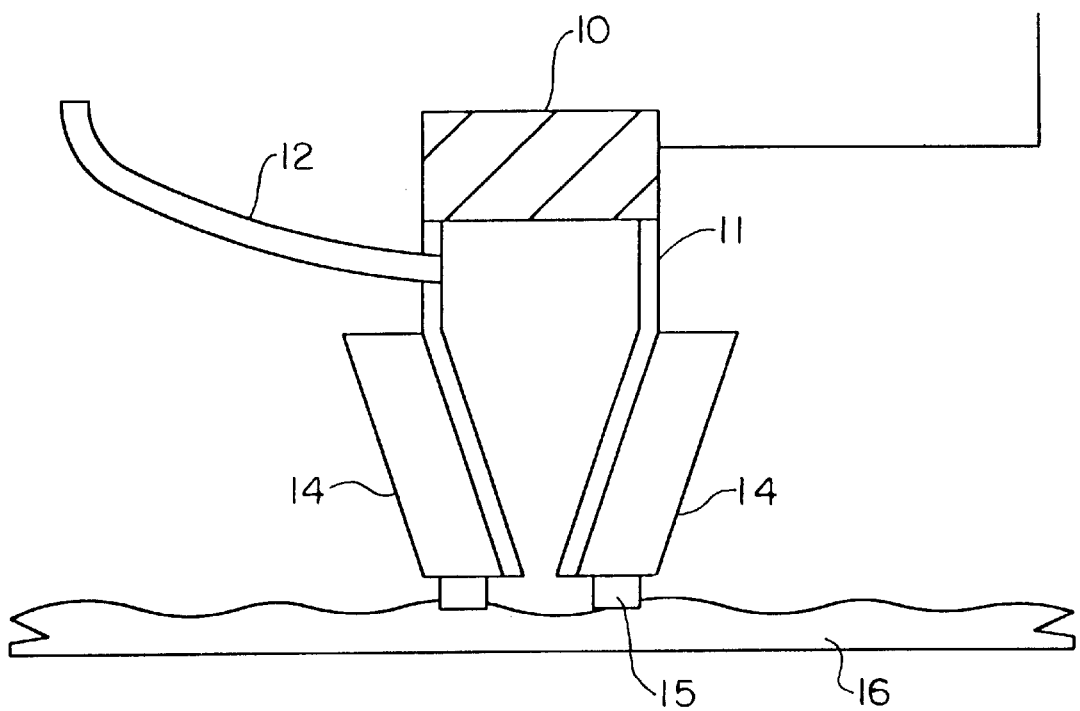
FIG. 1 is a diagram of the focused transducer which is screwed into a hollow cone-like structured called a "bubbler" or "squirter"

At FIG. 1 is a liquid delay used to couple the sound to the culvert. This consists of a focused transducer 10 which is screwed into a hollow cone-like structure called a "squirter" 11 or "bubbler" 11. The "bubbler" 11 or "squirter" 11 is a hollow tapered cylinder with water confined and flowing in the center. Fluid 12 is injected into the side of the squirter 11 and exits in a stream at the tip of the cone, along its axis, which is coincident with the direction of propagation of the ultrasonic pulse emanating from the transducer 10. This fluid 12 provides a path for the propagating ultrasonic wave. A rubber stopper 14 was adapted and machined for the squirter 11, such that the squirter 11 fits inside it, with its cone tip terminating just below the top of the stopper 14. The stopper 14 has a channel at its tip to allow the water to escape, since a continuous stream of water is supplied to the squirter 11 to couple the sound. This allows the operator to apply some pressure on the squirter 11, and the water to escape, and thus more easily stabilize the position against the culvert wall. The rubber tip, due to its flexibility, allows the squirter 11 direction to be adjusted slightly with respect to the culvert wall 16 under light hand pressure, as it is pressed against the wall 16 when the technician is in the process of "searching" for a good echo which can be measured. The "searching" for a good echo requires the technician to look at the ultrasonic signals on an oscilloscope. The technician would adjust the position of the "squirter assembly" to maximize the echoes from the back surface of the culvert wall 16. A magnet 15 is also incorporated in the rubber stopper 14. This allows the operator to temporarily affix the squirter 11 to the culvert wall 16 once the ultrasonic echoes have been maximized. The operator's hands are free to do other tasks which may arise.

Figure 2:
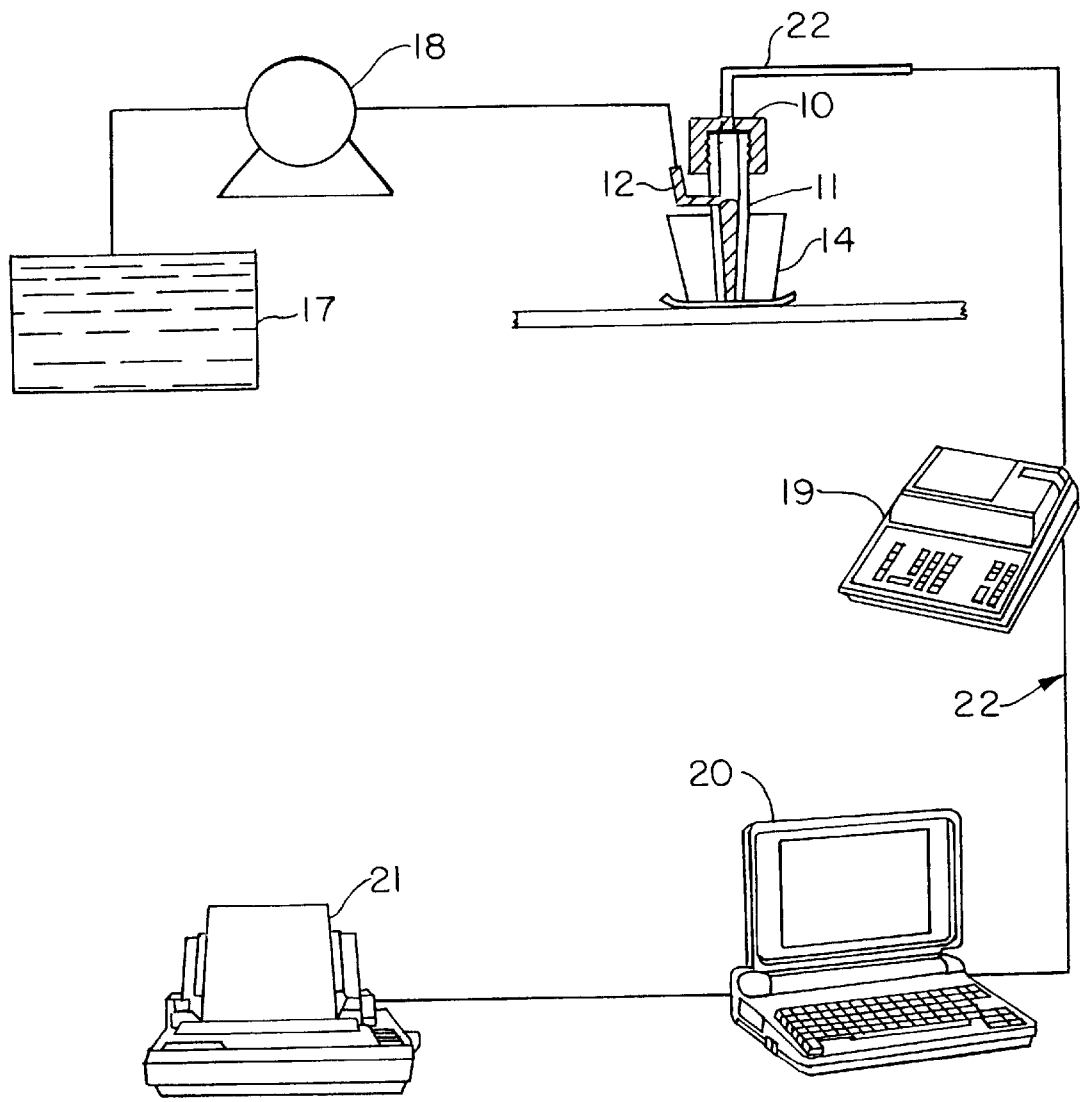
FIG. 2 is a schematic diagram of the proposed system for culvert thickness determination.

FIG. 2 shows the block diagram of the system to be used for the measurement of the culvert thickness. The water tank 17 is used to store the liquid utilized for couplant and the pump 18 can be either electrical/manual or other devices which assures that the water stream in the squirter/bubbler 11 is bubble free. The squirter 11 (or bubbler, the name is interchangeable) can be the commercially available Panametrics B120 bubbler with a 3/16 inch cone opening. The transducer 10 can be the commercially available, 1/8 inch diameter Panametrics V316-B focused transducer with a 20 MHz center frequency and a 0.75 inch point target focal distance. A spherically focused transducer is commonly used to improve sensitivity. A suggested UT ultrasonic transducer instrument 19 is the Panametrics 25DL which connects to a portable PC computer 20 using a RS-232 line 22. The computer 20 acts as an oscilloscope to view the ultrasonic signals and as a data storage unit. A printer 21 can also be used to print results.

Figure 3:
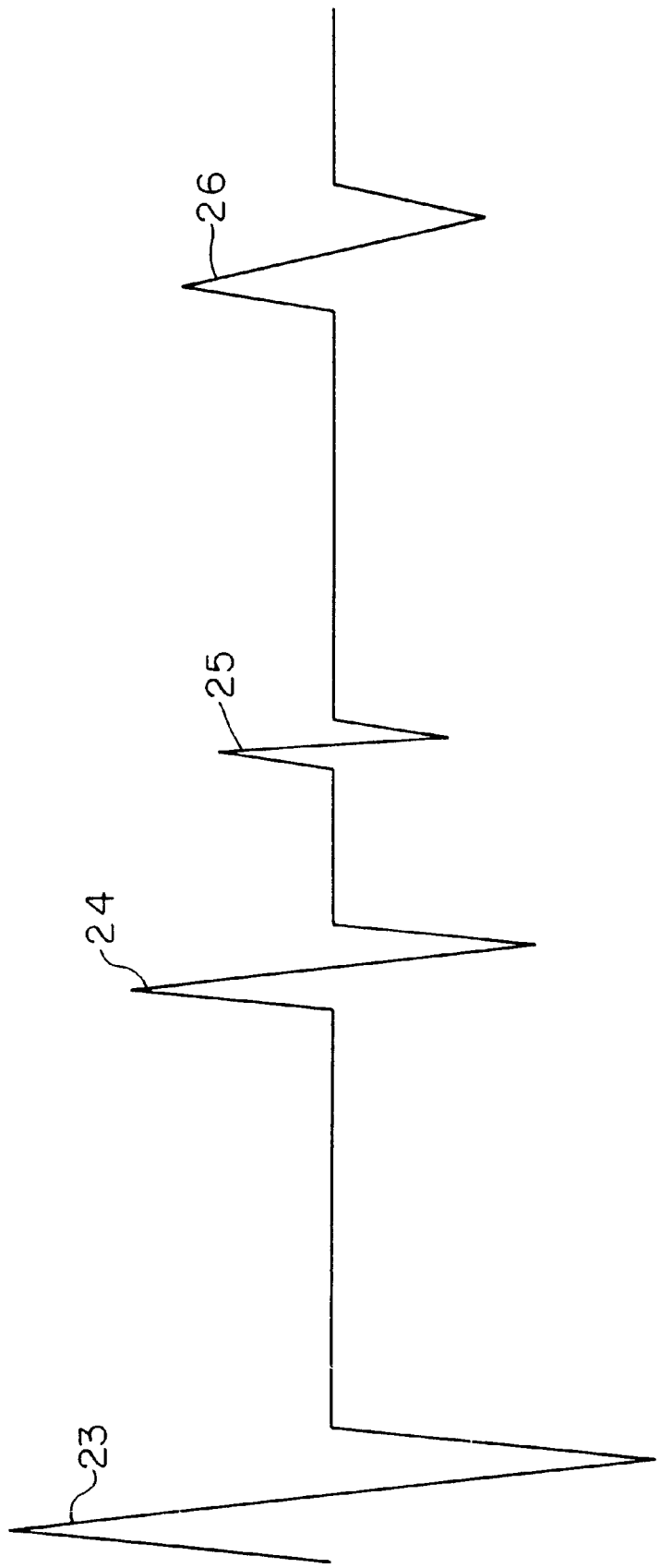
FIG. 3 is a schematic of the time of arrival of various echoes.

FIG. 3 gives a schematic representation of the echo voltages which appear on an oscilloscope screen, as well as in the counting circuits. Two significant improvements were achieved here. The liquid stream in 12 of the squirter 11 causes the return echo time to be displaced with respect to the "main bang" 23, since the ultrasonic signal must travel through the liquid delay before and after passing through the culvert wall 16. The return time which is now relevant can be measured between the first interface echo 24 and the first culvert back echo 25. The second interface echo 26 is not used in the measurements and would limit the maximum thickness of the culvert which could be measured. The commercial ultrasonic pulser-receiver-counter combination has the very useful feature in that it has the ability to measure the time interval between these two echoes. Further, the display indicates the starting and end point of the time interval measured. This is significant, in that the technician can check the echo train so that the correct reading is taken. In this way any thickness obtained would not be a data-reading artifact but measurements of appropriate times for visually confirmed echoes.

The other feature of this invention is a generic telemetry system (not shown), which helps to locate the position of the transducer when the thickness measurement is made. The thickness data, and the position of the transducer in the culvert can then be recorded and stored together and then plotted out at the end of the examination. In this way the record obtained at given time intervals can be compared, and the required action taken, or measurement intervals determined.

The measurement procedure is as follows:

To obtain the thickness from a time measurement, the velocity of sound in the culvert 16 material (steel) has to be obtained as well as any time offset due to electronic delay. The time measurement is described as follows:

$$t = t_{OFF} + \frac{2x}{v} \quad (1)$$

where t is the time measurement, $t_{OFF}$ is the offset, x is the thickness of the sample and v is the sound velocity. By measuring the time delay on two standards made of the same material of the culvert, the offset and the velocity can be measured. Assuming that t1 and t2 are the time delay measurements performed on the two standards of thickness x1 and x2, respectively, the offset and velocity are calculated as follows:

$$v = 2\left(\frac{x2 - x1}{t2 - t1}\right) \quad (2)$$

$$t_{OFF} = \frac{x2 \cdot t1 - x1 \cdot t2}{x2 - x1} \quad (3)$$

The thickness is thus obtained using the measured delay t and the following equation:

$$\text{thickness} = \frac{v}{2} \cdot (t - t_{OFF}) \quad (4)$$

At its simplest, the technician can carry a portable spray water container, similar to that which a gardener would use, strapped on his/her back. Any time a measurement is desired, the sprayer is activated and the fluid runs through the squirter 11 to the culvert surface 16 thus providing a couplant.

To provide the position for the transducer when measurements are made, one may install two telemetry distance measuring sources at two randomly selected points to serve as reference points on the culvert 16 at its opening. If the two sources are ultrasonic then they can emit pulses which can be received at the squirter 11, and the position of the squirter 11 on the culvert 16 can thus be defined. When thickness data is taken, the thickness and the position can thus be recorded and stored in the systems memory. The data can thus be made available in a hard copy for examination and comparison purposes, at a later time.

To obtain the culvert thickness, it has to be cleaned of encrusted scale and rust. This may be accomplished by a portable grinder with an appropriate small abrasive wheel. The surface is cleaned and incidentally smoothed with extremely mild material removal, to the point where only the culvert faces the "bubbler" and the surface is adequately smooth so that data can be obtained. Any manual or automatic surface cleaning procedure can be useful in increasing the accuracy and sensitivity of the measurements.

One can now apply the bubbler 11 configuration to culvert wall 16 and adjust the bubbler 11 to obtain the optimum echo. A switch is used to record data and position.

Figure 4:
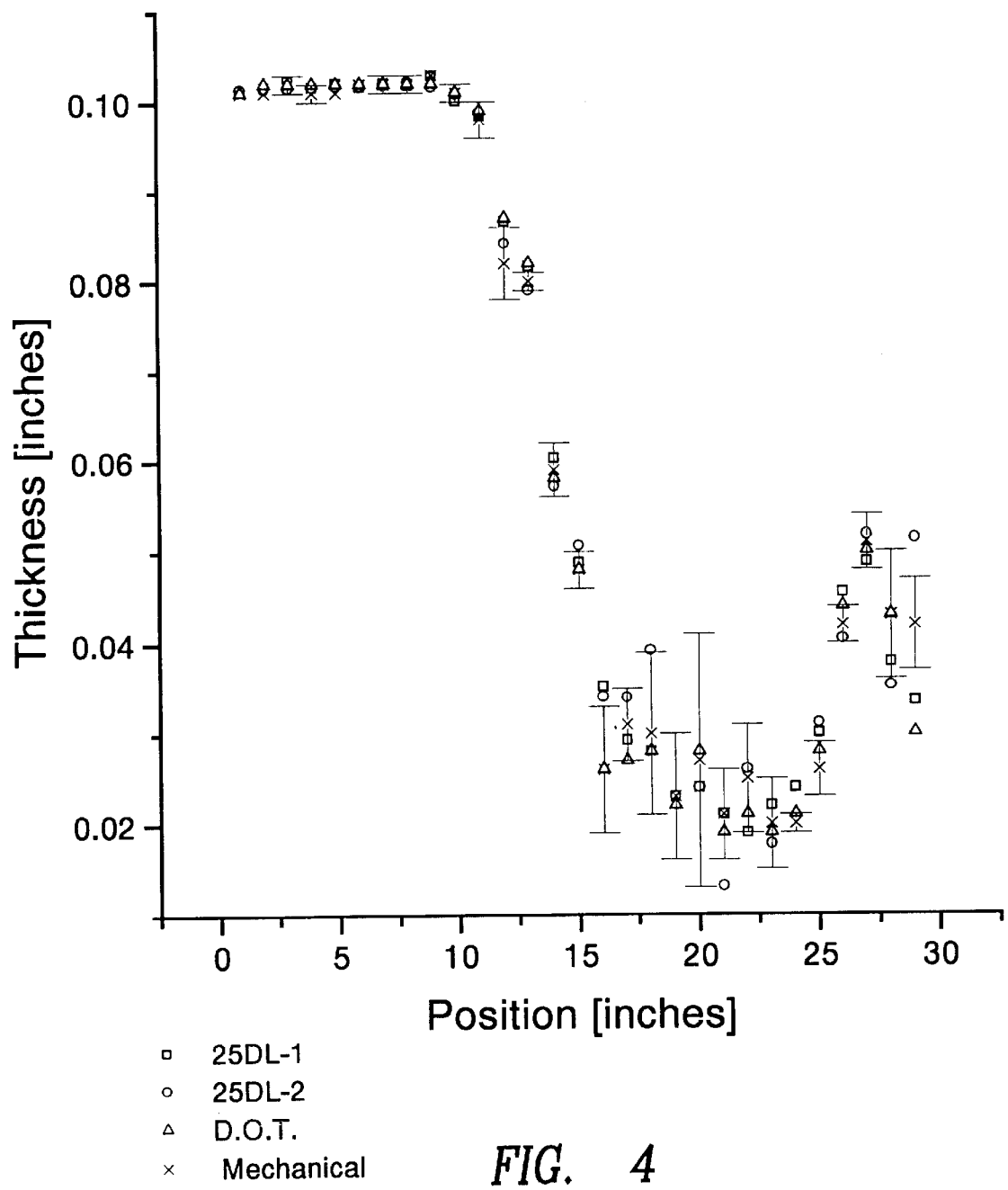
FIG. 4 is a plot of thickness data obtained from a culvert strip showing dangerous thinning and validation of the measurements taken by ultrasonic vis-a-vis mechanical measuring micrometers.

FIG. 4 depicts data taken from a 30 in. long strip, 2 in. wide, cut from a culvert 16 such that the long portion of the strip corresponds to the circumferential direction in the culvert 16. The strip also showed the orange-peel effect. FIG. 4 shows four data sets. 25DL-1, 25DL-2 are data taken by two different individuals with the ultrasonic system described herein. D.O.T is data taken with flat anvil micrometers and mechanical data taken with point-tip micrometers instead of flat anvils. The latter were able to measure thicknesses at a point instead of over an area. Because of the orange-peel effect, the thickness varied and the vertical bars indicate the range of thickness of the latter "point" measurements with the cross giving the average of the latter. FIG. 4 shows that under these circumstances the four types of data are in agreement. The ultrasonic technique here proposed was thus validated.

While particular embodiments of the present invention have been illustrated and described herein, it is not intended that these illustrations and descriptions limit the invention. Changes and modifications may be made herein without departing from the scope and spirit of the following claims.

What is claimed is:

1. A method of measuring the wall thickness of a component dimension of in-ground culverts, below and above the water line, to which sound waves are coupled comprising:

providing said in-ground culvert having said component dimension to which said sound waves are coupled;

providing a telemetry system which locates the position where the said sound waves are coupled and the measurements are taken of said components division of the said in-ground culvert allowing the record obtained at given time intervals to be compared and the measurement intervals determined, wherein the telemetry system comprises two telemetry distance measuring sources installed at two defined points in the said culvert at its opening;

transmitting a sound wave over a period of time through said in-ground culvert;

means for cleaning and smoothing the surface of the culvert in the vicinity where measurements are to be taken;

providing a liquid delay to couple the sound wave to the said in-ground culvert;

repeatedly searching for the optimum ultrasonic echoes which pass through the said in-ground culvert walls;

measuring the return times of the ultrasonic echoes; and calculating the thickness of said in-ground culvert by using the known velocity of the said coupled sound waves and measured return time of the ultrasonic echoes on a computer using the equations $$t = t_{OFF} + \frac{2x}{v} \quad (1)$$

$$v = 2\left(\frac{x2 - x1}{t2 - t1}\right) \quad (2)$$

$$t_{OFF} = \frac{x2 \cdot t1 - x1 \cdot t2}{x2 - x1} \quad (3)$$

$$\text{thickness} = \frac{v}{2}(t - t_{OFF}) \quad (4)$$

where t is the time measurement, $t_{OFF}$ is the offset, x is the thickness of the sample and v is the sound velocity and where t1 and t2 are the time delay measurements performed on the two standards of thickness x1 and x2.

2. A system for measuring the wall thickness of a component dimension of in-ground culverts, below and above the water line, to which sound waves are coupled, comprising:

providing said in-ground culvert having said component dimension to which said sound waves are coupled;

a telemetry system which locates the position where the said sound waves are coupled and the measurements are taken of said components division of the said in-ground culvert allowing the record obtained at given time intervals to be compared and the measurement intervals determined, wherein the telemetry system comprises two telemetry distance measuring sources installed at two defined points in the said culvert at its opening;

a source of sound waves for transmission over a period of time through said in-ground culvert;

means for cleaning and smoothing the surface of the culvert in the vicinity where measurements are to be taken;

a liquid delay to couple the sound wave to the said in-ground culvert;

manual searching for the optimum ultrasonic echoes which pass through the said in-ground culvert walls;

means for measuring the return times of the ultrasonic echoes; and means for calculating the thickness of said in-ground culvert by using the known velocity of the said coupled sound waves and measured return time of the ultrasonic echoes on a computer using the equations $$t = t_{OFF} + \frac{2x}{v} \tag{1}$$

$$v = 2\left(\frac{x2 - x1}{t2 - t1}\right) \tag{2}$$

$$t_{OFF} = \frac{x2 \cdot t1 - x1 \cdot t2}{x2 - x1} \tag{3}$$

$$\text{thickness} = \frac{v}{2}(t - t_{OFF}) \tag{4}$$

where t is the time measurement, $t_{OFF}$ is the offset, x is the thickness of the sample and v is the sound velocity and where t1 and t2 are the time delay measurements performed on the two standards of thickness x1 and x2.

* * * * *